United States Patent [19]

Miller, Jr.

[11] Patent Number: 5,268,308
[45] Date of Patent: Dec. 7, 1993

[54] IMMUNOASSAY FOR PYRIDOSTIGMINE

[75] Inventor: Russell L. Miller, Jr., Washington, D.C.

[73] Assignee: Howard University, Washington, D.C.

[21] Appl. No.: 335,590

[22] Filed: Apr. 10, 1989

[51] Int. Cl.$^5$ ................. G01N 33/531; G01N 33/534; G01N 33/53; A61K 35/14
[52] U.S. Cl. ..................................... 436/542; 436/543; 436/545; 436/547; 436/804; 424/88; 530/389.8
[58] Field of Search ............... 436/542, 519, 536, 543, 436/823; 435/7, 7.1; 514/346

[56] References Cited

U.S. PATENT DOCUMENTS

| | | | |
|---|---|---|---|
| 3,809,782 | 5/1974 | Spector | 236/542 |
| 4,151,268 | 4/1979 | Spector | 424/1 |
| 4,196,185 | 4/1980 | Focella et al. | 424/1 |
| 4,785,080 | 11/1988 | Farina et al. | 530/402 |

OTHER PUBLICATIONS

Meyer et al. J. Pharma Exp. Therap. 247(2):432 (1988).
Miller et al. Pharmac. Res. 21(4):359 (1989).
Shih et al. Anal. Lett. 19(9.10):1137-51 (1986).
Kluwe et al. Proceedings of 6th Medical Defen. Bios Review Columbia. Md. (1987).
Ellin et al. J. Chromato. 228P235-44 (1982).
Carter et al. Neurology 30:732-39 (1980).

*Primary Examiner*—Robert A. Wax
*Assistant Examiner*—Miguel Escallon
*Attorney, Agent, or Firm*—Kenyon & Kenyon

[57] ABSTRACT

A radioimmunoassay for pyridostigmine in biological fluids. The method disclosed can detect 250 pg of pyridostigmine per ml of biological fluid using 0.1 ml of biological fluid. The antibody used in this method is raised from an antigen produced by diazotizing para-aminobenzoic acid and reacting the diazotized material with pyridostigmine to form a pyridostigmine-hapten solution, which is then reacted with bovine serum albumen. The antibody used in the disclosed method has a cross-reactivity with the major metabolites of pyridostigmine of less than 2%.

6 Claims, 4 Drawing Sheets

IMMUNOASSAY FOR PYRIDOSTIGMINE

FIELD OF INVENTION

The invention relates to a immunoassay for pyridostigmine in biological fluids. More particularly, the invention relates to a sensitive and specific radioimmunoassay for pyridostigmine which involves producing an antibody for an pyridostigmine hapten-bovine serum albumin complex. The radioimmunoassay of this invention detects pyridostigmine quantities as low as 250 pg of pyridostigmine per 0.1 ml of body fluid.

BACKGROUND OF THE INVENTION

Pyridostigmine is a synthetic quaternary ammonium compound which occurs as a hygroscopic crystalline powder, freely soluble in water and alcohol. Being a carbamate, pyridostigmine has a characteristic odor, a bitter taste and is unstable in alkaline solutions. Aqueous solutions of pyridostigmine may be sterilizes by autoclaving. Pyridostigmine has been found to have a profound effect on the neurological functions of humans and other mammals.

Pyridostigmine is a reversible cholinesterase inhibitor which prevents the hydrolysis of acetylcholine by competing with acetylcholine for attachment to acetylcholinesterase. Acetylcholine is a neurotransmitter stored in vesicles where it isprimarily released by nerve impulses. The vesicles migrate towards the terminal synaptic membrane during nerve stimulation and disgorge acetylcholine by exocytosis Upon release fromthe cholinergic nerve endings, acetylcholine is inactivated by enzymatic degradation. The inactivation is accomplished by the hydrolysis of acetylcholine by cholinesterase. The specific cholinesterase for acetylcholine, acetylcholinesterase, is quite efficient—one molecule of the enzyme is able to hydrolyze $3\times10^5$ molecules of acetylcholine per minute.

Because a pyridostigmine-acetylcholinseterase enzyme complex hydrolyzes at a much slower rate than the corresponding acetylcholine-acetylcholinesterese enzyme complex, acetylcholine accumulates at the cholinergic synapses. Due to the reversible nature, i.e., uncoupling, of the pyridostigmine-acetylcholinestebase complex, pyridostigmine appears to facilitate the transmission of impulses across the myoneural junction In other words, the introduction of pyridostigmine produces generalized cholinergic responses. And while pyridostigmine has a direct cholinomimetic effect on skeletal muscles, because of its quaternary ammonium structure, moderate doses of pyridostigming usually do not effect the central nervous system.

Reversible cholinesterase inhibitors, such as pyridostigmine, have been proposed as antidotes to nerve agents used in chemical warfare. Many nerve agents, including sarin, soman, tabun and VX, are organ-phosphorous compounds which, while liquid at room temperature, are readily vaporized under normal atmospheric conditions. The extreme toxicity of such organo-phosphorous compounds are related to their short-lived, but irreversible destruction of the functioning of nerves and organs. By phosphorylating acetylcholinesterase, organophosphorous compounds such as varin form stable, irreversible Complexes with acetylcholinesterase. The formation of such stable complexes permanently prevent the normal function of acetylcholinesterase, i.e., the termination of acetylcholine actions at synaptic, particularly neuromuscular, junctions. Since the enzyme is completely and permanently prevented from binding with acetylcholine, the acetylcholine quickly accumulates at receptor sites to a degree sufficient to produce loss of function in target nervos and organs.

From animal studies, it has been proposed that nerve agent toxicity can be prevented by the preadministration of a short acting, reversible cholinesterase inhibitor such as pyridostigmine. The pyridostigmine would temporarily bind acetylcholinesterase in the tissue which would prevent its phosphorylation by the nerve agents and the resulting irreversible inactivation of the active site of the acetylcholinesterase.

Moreover, there are several clinical uses for reversible cholinesterase inhibiting agents such as pyridostigmine. Pyridostigmine is used to improve muscle strength in the symptomatic treatment of mysthenia gravis. Parental pyridostigmine is also useful in reversing of the effects of nondepolarizing neuromuscular blocking agents, e.g., tubocurarine, metocurine, gallamine or pancuronium, after surgery. Recently, cholinesterase inhibitors have been used in an attempt to reverse certain regenerative disorders of the central nervous system. It has been suggested that since cOgnitive changes observed during the aging process, e.g., Alzheimer's syndrome, may be related to gradual reductions in acetylcholine in various parts of the brain, the administration of pyridostigmine might help reduce or reverse the observed cognitive changes.

Results obtained from the administration of oholinesterase inhibitors such as pyridostigmine to maintain, restore or increase acetylcholine levels in patients, including those with Alzheimer's syndrome, have been equivocal. A primary problem encountered with the clinical use of pyridostigmine has been that it is toxic at levels very close to those which produce therapeutic results. For example, in certain patients pyridostigmine has been associated with adverse effects typical of exaggerated responses to parasympathetic stimulation including adverse muscarinic effects such as nausea, vomitin , diarrhea, miosis, excessive salivation and sweating, abdomimal cramps, bradycardia, bronchial secretion and bronchospasm. Other side effects of pyridostigmine include generalized weakness, muscle cramps, fasciculation, hypotension, and if administered intraveneously, thrombophlebitis. A substantial over administration of pyridostigmine causes cholinergic crisis leading to death.

Despite its relatively long clinical use, relatively little is known about the pharamacokinetic paramenters, i.e., the change in concentration at various sites, including absorption, distribution, metabolism and excretion, of pyridostigmine in man. The death of information is due primarily to the lack of a satisfactory analytical method for measuring low concentrations of pyridostigmine in biological fluids.

There are several reasons why analytical methods for measuring pyridostigmine in biological fluids have been unsatisfactory. The amounts of pyridostigmine to be measured are extremely low, which means that any analytical method must be sufficiently sensitive to detect extremely low levels of pyridostigmine. Moreover, the extensive in vitro hydrolysis of pyridostigmine which may take place in biological solutions, particularly in plasma and blood, exacerbates the problems associated with measuring small quantities of pyridostigmine. Consequently, analytical techniques such as paper chromatography, spectrophotomety, gas chromatography and high pressure liquid chromatography have proven to be unsatisfactory.

While immunoassays are often used to determine the minute quantities of drugs in biological fluids, heretofore an immunoassay for determining the presence of pyridostigmine in such fluids has been unavailable. The pyridostigmine molecule is too small to stimulate the immune systems of animals normally used to produce antibodies. The problem is complicated by the fact that the pyridostigmine molecule does not contain any functional groups which are usually necessary for a molecule to be linked to a protein immunogen. Of course, to be effective, an immunogen for pyridostigmine has to be sufficiently selective to avoid cross reactivity with the metabolites of pyridostigmine.

It is therefore an object of the present invention to provide for a method for the determination of the amount of pyridostigmine in biological fluid.

It is another object of the present invention to provide an immunoassay for the determination of the amount of pyridostigmine in biological fluids.

Yet another object of the present invention is to provide an immunogen which after injection into animals will result in the production of antibodies for use in an immunoassay for the determination of pyridostigmine in biological fluids.

Still a further object of the present invention is to provide monoclonal and polyclonal antibodies which can be used to determine pyridostigmine in biological fluids.

A further object of the present invention is to provide for a method of measuring pyridostigmine in biological fluids which faoilitates the study of the pharmacokinetics of pyridostigmine.

Still another object of the present invention is to proVide for a reduction in the toxicity and other adverse side effects which results from the clinical use of pyridostigmine.

These and other objects of the present invention, as will become more readily apparent hereinafter, are achieved by the invention described herein below.

SUMMARY OF THE INVENTION

The invention provides a sensitive and specific radioimmunoassay (RIA) for pyridostigmine which detects quantities as low as 250 pg of pyridostigmine per ml of biological fluid, using a 0.1 ml sample of biological fluid, without extraction. The invention provides for an immunogen comprising a pyridostigmine-p-aminobenzoic acid (PABA)-bovine serum albumin (BSA) complex. The immunogen is made by first diazotizing PABA and then reacting it with pyridostigmine to form a pyridostigmine hapten. The hapten is then reacted with the BSA. The immunogen, as synthesized, is then administered to an animal and the resultant serum containing antibodies is harvested from the animal's blood. The harvested serum then is used in the RIA at a final dilution of 1:150.

Using the RIA of the present invention, the pharmacokinetics of pyridostigmine can be studied. The RIA of the present invention is extremely sensitive and accurate. For example, while detecting quantities as low as 250 pg of pyridostigmine per 0.1 ml of biological fluid, the major s metabolites of pyridostigmine do not cross-react with the antibodies raised in response to the pyridostigmine immunogen. The specificity of the RIA has been validated by using the high pressure liquid ohromatography (HPLC) method for pyridostigmine detection.

BRIEF DESORIPTION OF THE DRAWING

DETAILED DESCRIPTION OF THE INVENTION

Figure 1:
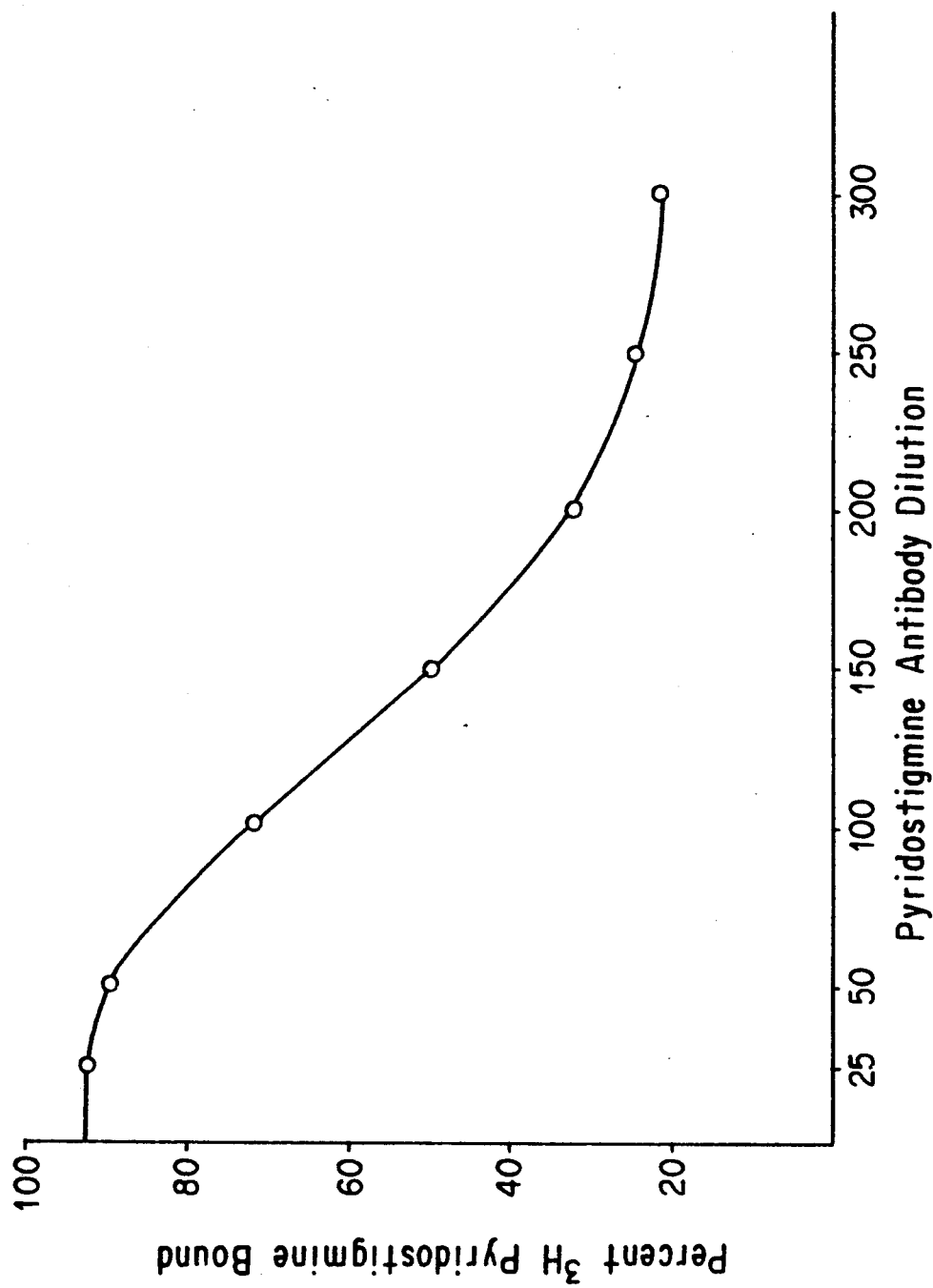
FIG. 1 is the antibody dilution curve for pyridostigmine.

Radioimmunoassay (RIA) is a sensitive procedure for quantitative in vitro measurement of drug levels in biological fluids. RIA is based upon the observation that unlabeled antigen and radioactive-labeled antigen compete to bind with antibody to the antigen in vitro. The essence of the pyridostigmine RIA, as embodied in the present invention, is that unlabeled pyridostigmine and radioactively labeled pyridostigmine compete to bind with antibodies to a pyridostigmine immunogen in an in vitro reaction mixture. All reaction mixtures, whether for standard curve construction or serum samples, contain set amounts of radioactively labeled pyridostigmine and antibodies to pyridostigmine, and a variable amount of pyridostigmine (standards or serum samples). The antibodies to pyridostigmine bind either with pyridostigmine or radioactively labeled pyridostigmine, with the binding to radioactively labelled pyridostigmine being dependent upon the amount of unlabeled pyridostigmine present. As the amount of pyridostigmine in the reaction mixture increases, the amount of radioactively labeled pyridostigmine that binds to the available pyridostigmine antibody decreases.

To assay the concentration of pyridostigmine in biological fluids, reaction mixtures are set up containing radioactively labeled pyridostigmine, antibody to pyridostigmine and a sample of biological fluid. The amount of radioactively labeled pyridostigmine bound to the pyridostigmine antibody is measured in counts per minute using a scintillation counter. The amount of pyridostigmine present then is determined from a standard curve. The standard curve is constructed by experimentally determining that when "X" amount of unlabeled pyridostigmine standard is introduced into the reaction, "A" amount of labeled pyridostigmine is recovered bound to pyridostigmine antibody; and when "Y" amount of unlabeled pyridostigmine is introduced into the reaction, "B" amount of labeled pyridostigmine recovered bound to pyridostigmine antibody, etc. From this data, the standard curve is constructed showing amounts of labeled pyridostigmine recovered bound to antibody versus unlabeled pyridostigmine present. Subsequently, when a sample of biological fluid with an unknown amount of pyridostigmine is assayed in the reaction mixture, and "A" amount of labeled pyridostigmine is recovered bound to pyridostigmine antibody, it is determined from the standard curve that "X" amount of pyridostigmine is present in the biological fluid sample.

The detailed description of the present invention can be more fully understood by the following detailed procedure for a specific embodiment of the invention. While the specific embodiment describes the invention in terms of polyclonal antibodies, it will be apparent to one skilled in the art that the present invention contemplates raising and utilizing monoclonal antibodies in the RIA disclosed therein.

DESCRIPTION OF A PREFERRED EMBODIMENT

As a first step in the RIA, a pyridostigmine immunogen was prepared. 68.57 mg (0.5 mmole) of paraaminobenzoic acid (PABA), obtained from Sigma Chemical Co., was dissolved in 2.0 ml of 1.0 N HCL, and the solution was cooled to 0°–4° in an ice bath. Similarly 34.5 mg (0.5 mmole) of sodium nitrite, also obtained from Sigma Chemical Co., was dissolved in 2.0 ml of ice-cold water. The dilute sodium nitrite was added dropwise to the PABA/HCI solution at 0°–4° C. with constant stirring, and the reaction was allowed to proceed for forty-five minutes at 4° C. with intermittent gentle stirring. 150 mg (0.57 mmole) of pyridostigmine from Hoffman LaRoche, Inc. was dissolved in a solution of 2.0 ml of water and 3.0 ml of 0.1 M sodium phosphate buffer. The pH of the diluted pyridostigmine was adjusted to 5.5 and the solution was cooled to 0°–4° C. The diazotized PABA solution was added dropwise to the pyridostigmine solution, with the pH maintained at 5.5 while stirred in an ice water bath. The reaction was allowed to proceed in the dark for 4 hours at 4° C.

50 mg (0.0074 mmole) Bovine serum albumin (BSA) from Miles Laboratories was added to the pyridostigmine hapten solution and the pH was adjusted to 5.5. Next, 200 mg of water soluble 1-ethyl-3-(3-dimethylaminopropyl) carbodiimide HCI, from Calbiochem, was dissolved in water and slowly added to the diazotized pyridostigmine. The reaction was allowed to proceed overnight at room temperature. The solution was dialyzed for 24 hours against 100 volumes of distilled water changing the solution every 6 hours; and then against 0.9 percent sodium chloride for 16 hours changing the solution every 4 hours. This immunogen solution was then measured, aliquoted, and stored at $-20°$ C.

Antibodies to the pyridostigmine-BSA immunogen were produced by injecting male New Zealand white rabbits. Prior to injection, the immunogen was emulsified with an equal volume of complete Freund's adjuvant, purchased from Difco Laboratories. The initial immunization consisted of 0.8 mg of protein injected intracutaneously into the back of the rabbits. Booster injections containing 0.8 mg of immunogen and incomplete Freund's adjuvant were administered every one or two months for the next seven months. Blood was collected one week after each booster injection from the central ear vein. The blood was allowed to clot at room temperature and then centrifuged at 1500×g for 15 minutes. The separated serum was stored frozen at $-20°$ C. until assayed for the presence of pyridostigmine antibody. The pyridostigmine-BSA complex proved quite immunogenic to the rabbits. After the third booster injection, the titer, i.e., the final dilution of the antiserum needed to bind 50% of added tracer (H-pyridostigmine), of the antisera Was 1:150. FIG. 1 is the antibody dilution curve for pyridostigmine.

In the assay procedure tritiated pyridostigmine having specificity of 76.3° Ci/mmole was used as tracer. The dilution of tracer, antisera and pyridostigmine standards were made using 0.01 M phosphate buffer containing 150 mM sodium chloride with a pH of 7.4.. The specificity of the antisera is such that in the assay procedure it is used at a final dilution of 1:150. Both standard and sample tubes were always analyzed in duplicate. The assay was carried out according to the protocol shown in. Table 1 with the reagents were added to the assay tubes in the order shown in. Table 1.

TABLE 1

| | Protocol for the Radioimmunoassay Procedure | | | |
|---|---|---|---|---|
| | Volume of Reagent Added (μl) | | | |
| Reagent | Standard Curve Tube | Zero Binding Tube | Nonspecific Binding Tube | Sample Tube |
| PBS (buffer) | 150 | 250 | 350 | 250 |
| Standards | 100 | — | — | — |
| ³H-Pryidostigmine | 50 | 50 | 50 | 50 |
| Diluted antiserum | 100 | 100 | — | 100 |
| Sample | — | — | — | 100 |
| Normal Plasma | 100 | 100 | 100 | — |
| Vortex and Incubate 3 hr at 4° C. | | | | |
| 100% Saturated Ammonium Sulfate | 500 | 500 | 500 | 500 |
| Centrifuge and Aspirate | | | | |
| 50% Saturated Ammonium Sulfate | 1000 | 1000 | 1000 | 1000 |
| Centrifuge and Aspirate | | | | |
| Distilled Water | 1000 | 1000 | 1000 | 1000 |

According to the protocol for the RIA of the present invention, after the addition of antisera, the contents of the tubes were mixed and incubated for 3 hours at 4° C. The antigen which bound to the antibody was separated by adding 100% saturated ammonium sulfate and centrifuging at 2500×g for 15 minutes. After aspiration of the supernatant, the precipitate was washed one time with 50% saturated ammonium sulfate; then the mixture was centrifuged and the supernatent removed. The precipitate was dissolved in 1.0 ml of distilled water, and the solution was transferred to a scintillation vial containing 10.0 ml of acquasol.

Figure 2:
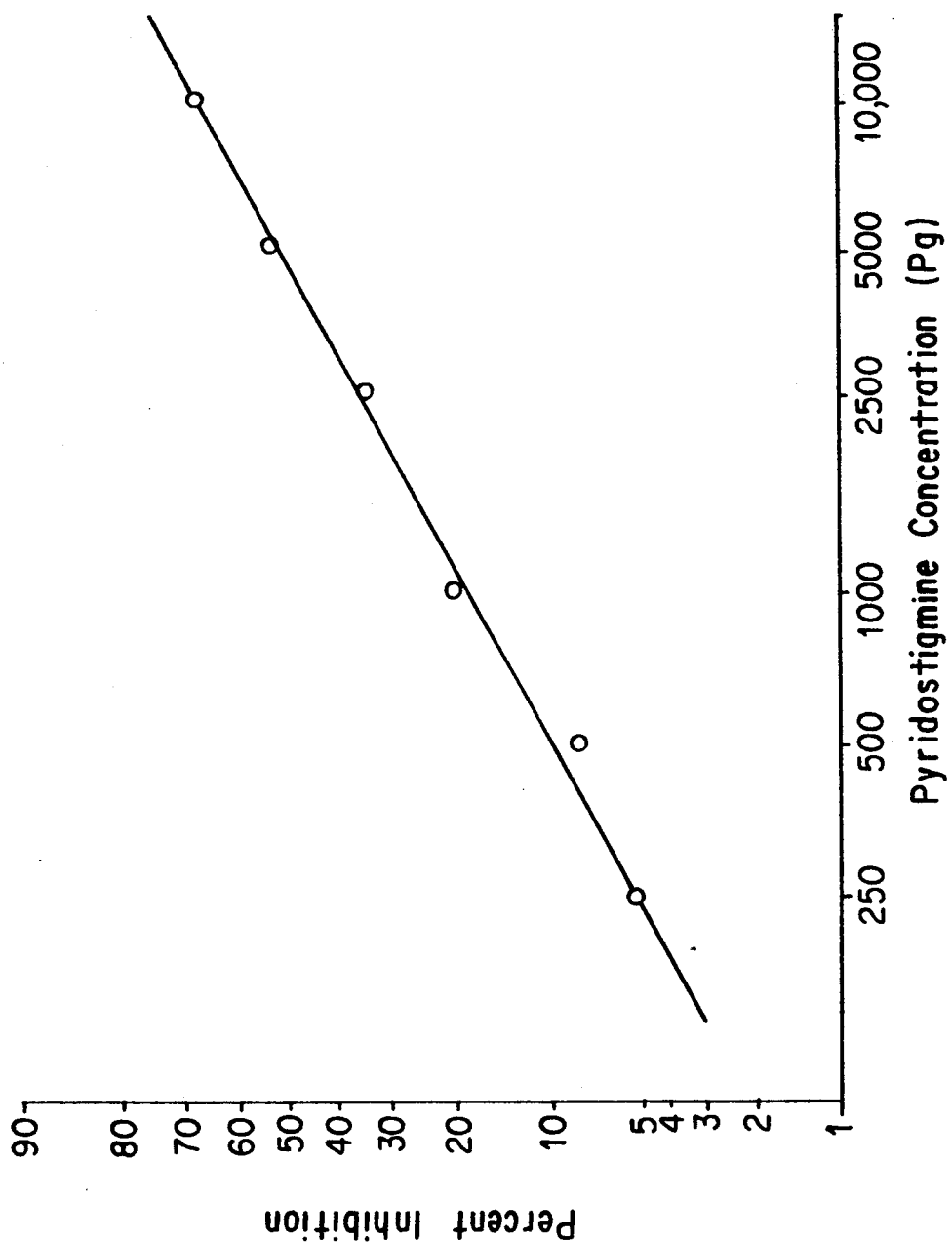
FIG. 2 is the standard linear dose-response (logit-log) curve for a specific polyclonal antibody of the present invention.
Figure 3A:
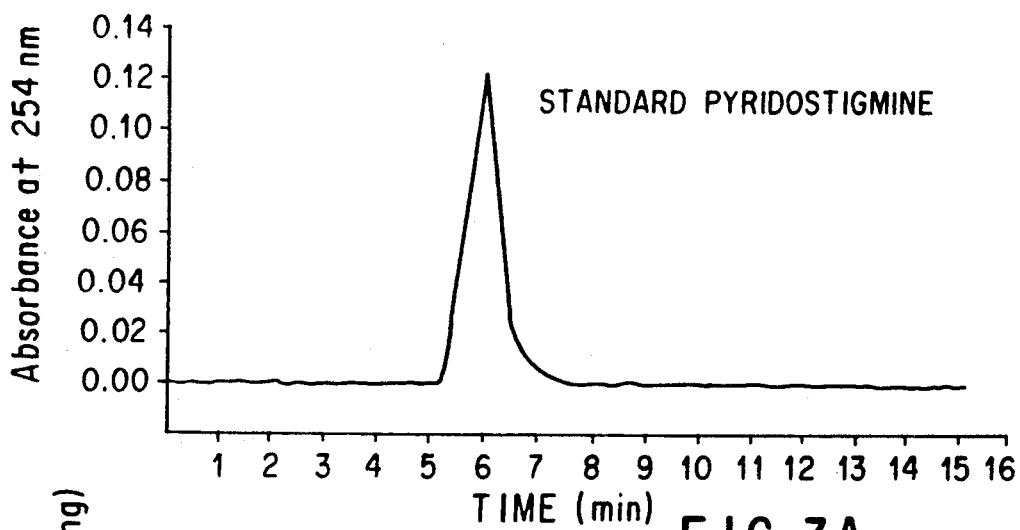
FIGS. 3A, 3B, 3C, 3D and 3E are a series of high pressure liquid chromotographs which confirm the specificity of the RIA of the present invention.
Figure 3B:
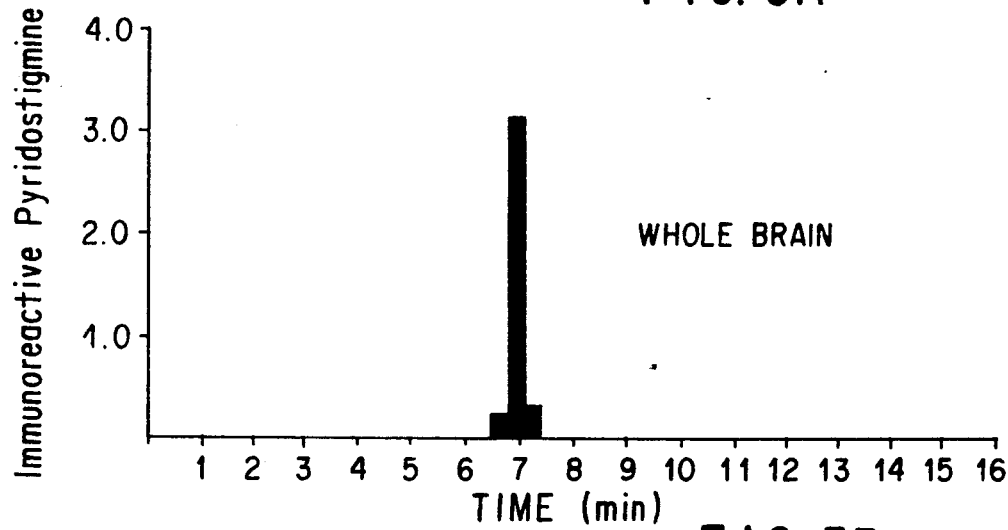
Figure 3C:
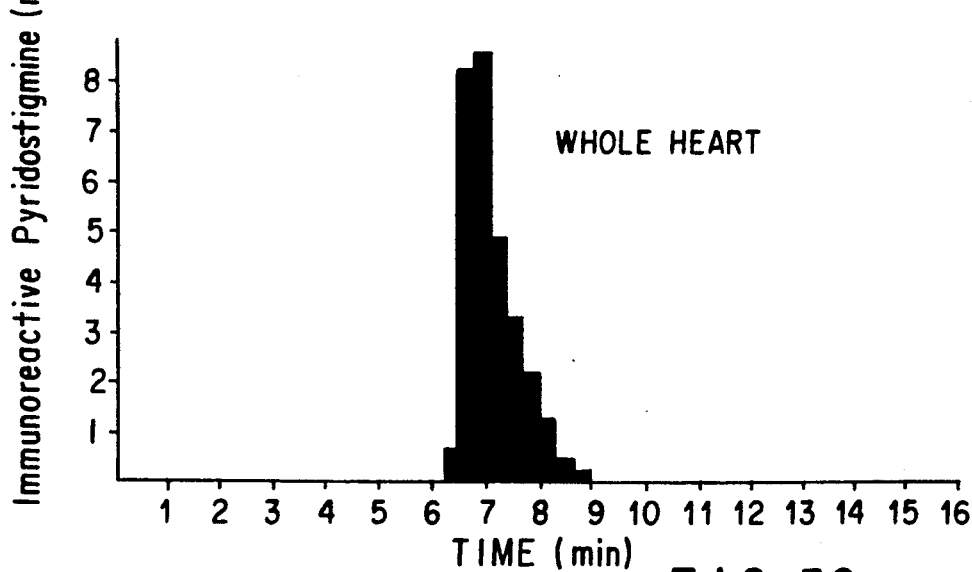
Figure 3D:
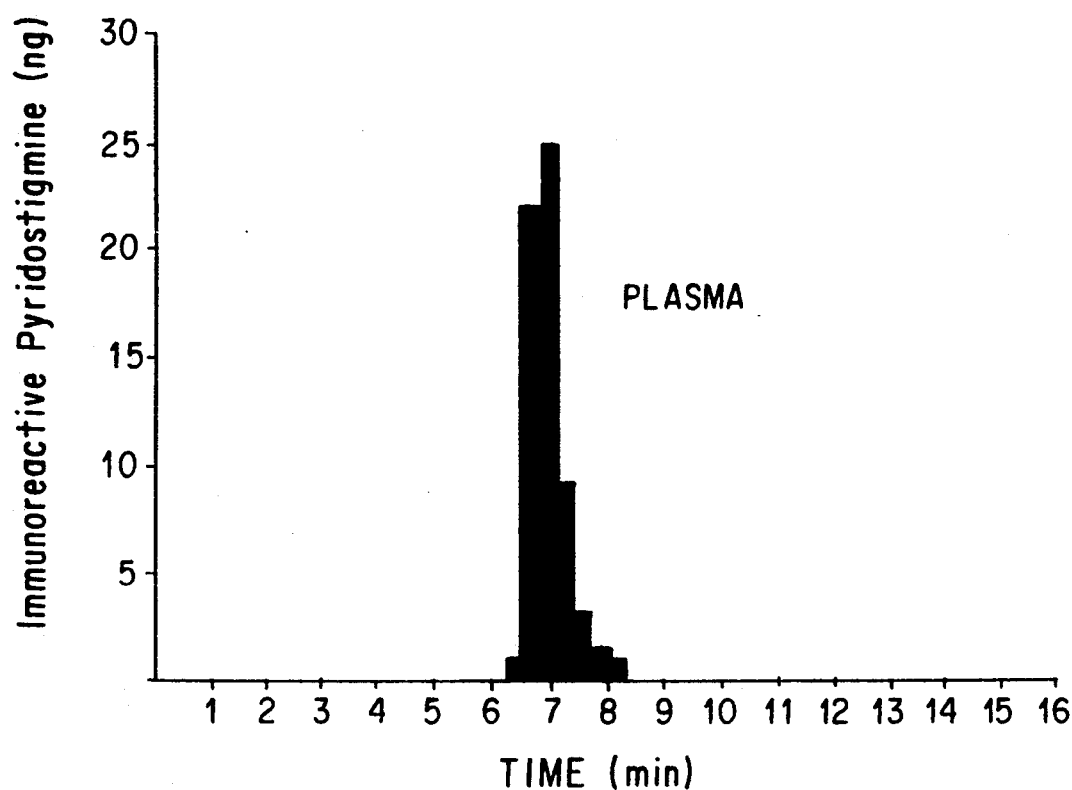
Figure 3E:
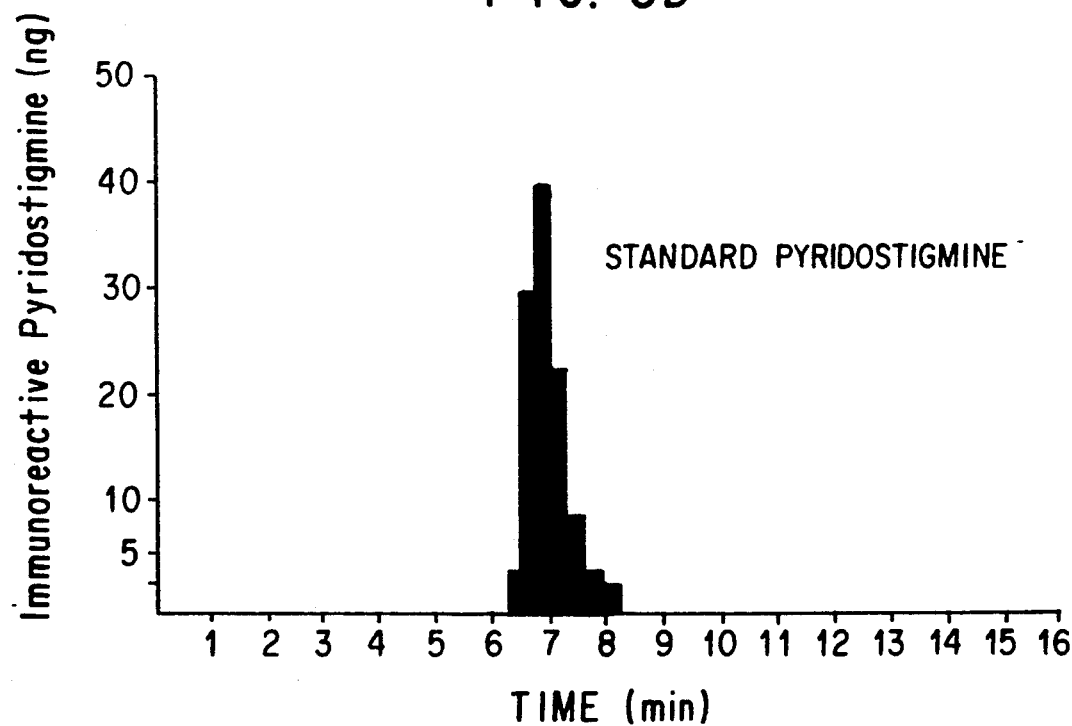

The radioactivity which was bound to the antibody was determined in counts per minute with a Beckman LS-3133P Liquid Scintillation Counter. FIG. 2 shows the standard dose response curve of the RIA for pyridostigmine when plotted on a logit-log scale. The concentration of pyridostigmine is plotted on the horizontal axis, while the percent inhibition of binding radioactively labeled is plotted on the vertical axis. About 250 pg per ml of pyridostigmine can be distinguished from zero pg. The useful range of the standard curve extends up to 10 ng per assay tube. The addition of 100 ul of normal human or rat serum or plasma had no effect on either the nonspecific binding or the standard curve. Concentrations of pyridostigmine in unknown samples were determined according to conventional calculations from the standard curve.

The antibodies of the present invention are highly specific. Cross-reactivity of various compounds with pyridostigmine antibody was determined in the RIA. Competition of the compounds with labeled pyridostigmine (5000 DPM) for antibody binding sites was determined arbitrarily at 50% inhibition ($IC_{50}$) of the pyridostigmine on the standard curve. Each compound was tested for cross-reactivity with the antibody. The maximum concentration of each compound tested was 500 ng.

TABLE 2

| Cross-Reactivity of the Pyridostigmine Antibody | |
|---|---|
| Compound | IC 50 (ng) |
| Pyridostigmine | 4 |
| Physostigmmine | >500 |

TABLE 2-continued

Cross-Reactivity of the Pyridostigmine Antibody

| Compound | IC 50 (ng) |
|---|---|
| Neostigmine | >500 |
| 3-Hydroxy-N-methyl-pyridostigmine | >500 |
| Atropine | >500 |
| Acetylcholine | >500 |
| Pralidoxime Chloride | >500 |

Table 2 presents the results of the tests of the reactivity of the metabolites of pyridostigmine with the pyridostigmine antibody. As shown in. Table 2, 4 ng of pyridostigmine produced a 50% inhibition of the binding of $^3$H-pyridostigmine to the antibody, while the up to 500 ng of the major metabolite and related compounds did not significantly inhibit the binding of labeled pyridostigmine to the antibody.

In order to validate the RIA of the present invention, a series of rat studies for the determination of pyridostigmine were conducted. Known amounts of pyridostigmine, ranging from 500 to 10000 pg, were added to normal rat serum and brain homogenates. These homogenates were then processed by the RIA of the present invention. The results of the RIAs versus known amount of added pyridostigmine, in which a percent recovery was calculated from the mean value of the measurement of twelve assay tubes at a particular dosage, are presented in. Table 3.

TABLE 3

Recovery of Pyridostigmine Added To Normal Rat Serum/Brain Homogenates

| Pyridostigmine Added (pg) | Pyridostigmine Measured (pg) Mean ± S.E.M. | Percent Recovery |
|---|---|---|
| 500 | 539 ± 40.24 | 108 |
| 1000 | 1005 ± 70.0 | 105 |
| 2000 | 2000 ± 60.0 | 100 |
| 5000 | 5012 ± 130 | 102 |
| 10000 | 10050 ± 120 | 101 |

As can be seen from. Table 3, the interassay and intraassay coeffioients of variation were always less than 1%. Moreover, non-specific binding appeared to be less than 2% and no blank effect was observed.

To further validate the RIA and the antibody specificity of the present invention, additional rat studies were conducted. Male rats were housed two per cage at 23° C. with a twelve hour on-off light cycle. The animals were given food and water ad libitum. After sixty days, food was withheld for twelve hours. Then pyridostigmine was administered (1.0 mg. of pyridostigmine bromide in physiologic saline/Kg) intramuscularly to the rats weighing between 450 and 550 grams.

Groups of three animals were sacrificed by using inhalation anesthetic, Fluothane (0.01% thymol, w/w; and 0.00025% ammonia, w/w) Ayerst Laboratories, New York, N.Y. at various times after dosing, namely at 0, 5, 10, 15, 30, 60 minutes and at 2, 3, 4 and 6 hours. Blood was collected via heart puncture, and serum was separated by centrifugation at 2000 xg for 20 minutes. Table 4 gives the pyridostigmine level in the plasma of three male rats for each time interval as determined by the RIA of the present invention.

TABLE 4

Pyridostigmine (ng/ml) in the Rat Sera

| Time After Administration | ANIMALS | | | Mean ± S.D. |
|---|---|---|---|---|
| | #1 | #2 | #3 | |
| 0 | 0 | 0 | 0 | 0 |
| 5 min | 600 | 550 | NM | 575 ± 35.36 |
| 10 min | 450 | 470 | NM | 460 ± 14.14 |
| 15 min | 400 | 300 | 460 | 387 ± 80.83 |
| 30 min | 250 | 400 | 220 | 290 ± 96.44 |
| 60 min | 140 | 140 | 110 | 130 ± 17.32 |
| 2 hr | 24 | 25 | 15 | 21 ± 5.51 |
| 3 hr | 12 | 14 | NM | 13 ± 1.41 |
| 4 hr | 7.5 | 5 | 6.5 | 6 ± 1.26 |
| 6 hr | ND | ND | ND | — |

ND = not detected
NM = not measured.

The brain, fat, heart, muscle and spleen were also removed from the sacrificed rats. The organs from each time period were pooled and kept frozen at −85° C. until analyzed. In preparing tissue homogenates for analysis, tissue samples were first brought to room temperature. Next the tissue samples were washed with ice-cold saline, blotted dry, weighed and homogenized in an ice-cold solution (10 nM EDTA, 0.5%. Triton X, 150 mM sodium chloride, pH 7.4; 2:1, v/w) with a Biohomogenizer (from Biospect Products Inc., Bartlesville, OK), cooling the tubes with ice as needed. The suspension was centrifuged at 15,000 ×g for 30 minutes at 020 −4° C. The supernatant was collected, and the pellet was mixed once more (1:1, w/v) with the solution, and centrifuged as described earlier. The supernatants for like samples were combined. The RIA of the present invention was then followed to determine the amounts of pyridostigmine in the various rat organs. The results of the RIA are given in. Table 5.

TABLE 5

Pyridostigmine* in Various Rat Organs

| OR-GAN | TIME INTERVAL | | | | | | | | |
|---|---|---|---|---|---|---|---|---|---|
| | 5 min | 10 min | 15 min | 30 min | 1 HR | 2 HR | 3 HR | 4 HR | 6 HR |
| Brain | 3.63 | 7.65 | 6.32 | 6.11 | 5.06 | 4.63 | 3.92 | 3.55 | 2.62 |
| Fat | 5.98 | 8.11 | 15.37 | 9.05 | 8.69 | 6.46 | 5.73 | 3.26 | 2.91 |
| Heart | 43.78 | 57.5 | 70.4 | 75.96 | 78.29 | 52.4 | 48.57 | 23.11 | 8.52 |
| Muscle | 9.63 | 13.57 | 11.67 | 10.08 | 9.46 | 4.99 | 4.8 | 3.94 | 3.08 |
| Spleen | 10.35 | 6.26 | 6.15 | 4.44 | 2.48 | 2.40 | 2.03 | 1.92 | 1.86 |

*Values are expressed as ng/mg protein. [Protein measured according to Lowry, O.H. et al. J. Biol. Chem. 193: 262-275 (1951)]

In order to prove the speoificity of the antibody of the present invention, an HPLC analysis was conducted. For that analysis aliquots from the supernatants obtained from preparation of the rat tissue homogenates were dried in a vacuum centrifuge. Prior to the HPLC fractionation, the supernatants were further purified on Sep Pak $C_{18}$ cartridge (Waters Associates, Milford, MA). Similarly, the tissue extracts were clarified on $C_{18}$ cartridge (Sep Pak column). To prepare the column 5 ml of acetonitrile followed by 15 ml of deionized water were passed through the column. The tissue extracts (1-2 ml) were passed through the Sep Pak column within 30-40 seconds. After washing the column with 5 ml water and 5 ml methanol and removal of methanol with air, elution was accomplished with 2 ml 0.2 mol/L acetic acid in methanol/water (5:1, v/v). The elute was concentrated in a vacuum centrifuge and resuspended in 0.3 ml of mobile phase (see mobile phase for HPLC). The suspension was filtered through a Millipore filter system (Millipore Corp., Bedford, MA) consisting of a thick prefilter (AP type) in series with a HA 0.45 um filter (to remove perticulate matter) and a 100 ul aliquot was injected.

The HPLC system consisted of Waters Associates Model 204 liquid chromatograph equipped with Model 441 absorbance deteotor, two model 6000 A pumps, a U6K injector, a model 720 system controller, an Omni Scribe recorder (Houston Instruments, Houston, TX), a model cygnet Fraction collector (ISCO, Lincoln, NE) and a 25 cm of u Bondapak/$C_{18}$ column (Water Associates, Milford, MA).

The mobile phase was prepared according to Breyer-pfaff et. al. (1) and composed of 0.75% acetonitrile, 7% 2-propanol, and 92.25% of an aqueous buffer containing 10 mmol/L sodium dihydrogen phosphate, 10 mmol/L sodium butanesulfonate, 2.5 mmol/L tetramethylammonium chloride, and sufficient 0.5 mmol/L sulfuric acid to adjust pH to 2.8.. The buffer was degassed by a combination of sonication and reduced pressure. A fixed Wavelength detector sets a 254 nm, the flow rate was 1.0 ml/ml, and the retention was 8.1 minutes for authentic pyridostigmine. The samples eluting from the column were collected every 20 seconds using the fraction collector. The solvent was evaporated and samples were assayed for pyridostigmine by radioimmunoassay. The antibody only bound to material in the fractions which came off the column at the time that the standard pyridostigmine was eluted. FIG. 3 consists of a series of high pressure chromatographs which confirm the specificity of the RIA of the present invention.

I claim:

1. A process for determining the concentration of pyridostigmine in a sample of biological fluid which comprises
   a. mixing said sample with an antibody for pyridostigmine, said antibody being formed from an antigen consisting essentially of pyridostigmine-p-aminobenzoic acid bonded to an immunogenic carrier material to an acidic pH;
   b. measuring the extent of binding between said antibody and pyridostigmine in said sample, and
   c. comparing the measured extent of binding between said antibody and pyridostigmine in said sample with a known quantitative relationship between an extent of binding and a specific concentration of pyridostigmine.

2. The process of claim 1, wherein said immunogenic carrier material is bovine serum albumin.

3. The process of claim 1, wherein said antigen is produced by a process which comprises
   a. diazotizing para-aminobenzoic acid by reacting it with hydrochloric acid and sodium nitrate,
   b. reacting said diaxotized para-aminobenzoic acid with pyridostigmine to form pyridostigmine-hapten solution, and
   c. reacting said pyridostigmine-hapten solution with bovine serum albumin.

4. The process of claim 1, wherein measurement of the extent of binding is effected by mixing a sample of pyridostigmine labeled with a radioactive isotope with the antibody to effect binding of pyridostigmine with said antibody, separating said bound material to said antibody and counting the amount of bounded radioactive isotope.

5. The process of claim 4, wherein said radioactive isotope is tritium.

6. A process for determining the concentration of pyridostigmine in a sample of biological fluid, sufficiently sensitive to detent 25 pg of pyridostigmine per 0.1 ml of biological fluid which comprises
   a. mixing said sample with an antibody for pyridostigmine, said antibody being formed from an antigen consisting essentially of pyridistigmine-p-aminobenzoic acid bonded to an immunogenic carrier material at an acidic pH;
   b. measuring the extent of binding between said antibody and pyridostigmine in said sample, and
   c. comparing the measured extent of binding between said antibody and pyridostigmine in said sample with a known quantitative relationship between an extent of binding and a specific concentration of pyridostigmine, wherein the cross reactivity of the antibody with major metabolities of pyrdostigmine is less than 2%.

* * * * *